(12) United States Patent
Dove et al.

(10) Patent No.: US 11,712,203 B2
(45) Date of Patent: Aug. 1, 2023

(54) SILICONE-BASED PATIENT-SIDE ADHESIVE IN A MEDICAL SENSOR

(71) Applicant: Covidien LP, Mansfield, MA (US)

(72) Inventors: Jacob Dove, Lafayette, CO (US); Derek L. Moody, Longmont, CO (US); Sarah L. Hayman, Boulder, CO (US); Linden A. Reustle, Milliken, CO (US); Shai Fleischer, Modiin (IL)

(73) Assignee: Covidien LP, Mansfield, MA (US)

( * ) Notice: Subject to any disclaimer, the term of this patent is extended or adjusted under 35 U.S.C. 154(b) by 221 days.

(21) Appl. No.: 16/904,689

(22) Filed: Jun. 18, 2020

(65) Prior Publication Data

US 2021/0393207 A1    Dec. 23, 2021

(51) Int. Cl.
*A61B 5/00* (2006.01)
*A61B 5/1455* (2006.01)
*C09J 183/04* (2006.01)

(52) U.S. Cl.
CPC ........ *A61B 5/68335* (2017.08); *A61B 5/1455* (2013.01); *A61B 5/14552* (2013.01); *A61B 5/0059* (2013.01); *A61B 2503/045* (2013.01); *A61B 2562/02* (2013.01); *C09J 183/04* (2013.01)

(58) Field of Classification Search
CPC .............. A61B 5/1455; A61B 5/14552; A61B 5/68335; A61B 5/02427
See application file for complete search history.

(56) References Cited

U.S. PATENT DOCUMENTS

| | | | |
|---|---|---|---|
| 9,636,057 B2 * | 5/2017 | Scheuing | A61B 5/6833 |
| 2011/0212325 A1 * | 9/2011 | Determan | A61L 24/043 |
| | | | 428/355 R |
| 2016/0022184 A1 | 1/2016 | Besko et al. | |
| 2016/0100780 A1 * | 4/2016 | Vastola | A61B 5/68335 |
| | | | 600/340 |
| 2017/0065190 A1 | 3/2017 | Green | |
| 2017/0081573 A1 * | 3/2017 | Kipke | A61L 26/0061 |
| 2019/0095172 A1 * | 3/2019 | Molesky | G06F 3/167 |

FOREIGN PATENT DOCUMENTS

| | | |
|---|---|---|
| WO | 2019195145 A1 | 10/2019 |
| WO | 2020092747 A1 | 5/2020 |

OTHER PUBLICATIONS

McNulty, A et al., "Use of Skin Strain Modeling to Assess Removal of Surgical Tape with Acrylate or Silicone Adhesive," poster presented at WoundCon 2021 Summer, Jul. 16, 2021. (Year: 2021).*

(Continued)

*Primary Examiner* — Eric F Winakur
(74) *Attorney, Agent, or Firm* — Shumaker & Sieffert, P.A.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes a silicone patient-side adhesive.

18 Claims, 4 Drawing Sheets

(56) References Cited

OTHER PUBLICATIONS

Grove, et al., "A Randomized and Controlled Compartison of Gentleness of 2 Me . . . : Journal of Wound Ostomy & Continence Nursing", Feb. 1, 2013, XP055843304, Retrieved from the Internet: url:https://journals.lww.com/wocnonline/Abstract/2013/01000/A_Randomized_and_Controlled_Comparison_of.8.aspx [retrieved on Sep. 21, 2021] abstract, 4 pgs.
International Application No. PCT/US2021/037723 International Search Report and Written Opinion dated Sep. 30, 2021, 16 pages (MD40368PCT).
Gary Grove et al., "An objective comparison of two pulse oximetry senors with different adhesive systems on healthy human volunteers bases on biophysical assessments", Skin and Resarch Technology, Wiley, 9 pp.
Laurie McNichol et al., "Medical adhesives and patient safety: state of the scienceconsensus statements for the assessment, prevention, and treatment of adhesive-related skin injuries", J Wound Ostomy Continence Nurs. 2013;40(4):365-380, 16 pp.
Catherine Noonan et al., "Skin integrity in hospitalized infants and children: a prevalence survey", Journal of Pediatric Nursing, 2006; 21(6):445-453, 9 pp.
Dale Gertsmann, MD et al. "Operational Evaluation of Pulse Oximetry in NICU Patients with Arterial Access". J of Perimatology 2003;23(5):378-383, 6 pp.
Paul D Mannheimer PD, The Light-Tissue Interaction of Pulse Oximetry. Anesthesia Research Society 2007; 105(6):S10-S17, 8 pp.
Fumio Tokumura et al. "Skin irritation due to repetitive application of adhesive tape: the influence of adhesive strength and seasonal variability", Skin Research and Technology 2005;11(2):102-106, 6 pp.
Richard I. Murahata et al., "Preliminary studies on the relationship among peel force, quantitative measures of skin damage and subjective discomfort", Skin Research Technology 2008;14(4):478-483, 7 pp.
Mike Waring et al., "A new methodology for evaluating the damage to the skin barrier caused by repeated application and removal of adhesive dressings", Skin Research and Technology 2013, 10 pp.
Mike Waring et al, "Cell attachment to adhesive dressings: qualitative and quantitative analysis", Wounds UK. 2008; vol. 4, No. 3, :35-47, 9 pp.
F Dreher et al., "Quantification of stratum corneum removal by adhesive tape stripping by total protein assay in 96-well microplates", Skin Res Technology 2005; 11: 97-101, 6 pp.
W Brockmann, et al. "Adhesion mechanisms of pressure sensitive adhesives", Int J Adhes Adhes. 1996; 16(2):81-86, 6 pp.
Deanne L. August et al., Pressure Injuries to the skin in a neonatal unit: Fact or Fiction, Department of Neonatology, The Townsville Hospital, Australia, Sep. 17, 2013, 9 pp.
Lund, Medical Adhesives in the NICU, UCSF Benioff Children's Hosptal, Oakland, CA, Newborn & Infant Nursing Reviews 14 (2014), 6 pp.
Leslie Altimier, The Neonatal Integrative Development Care Model: Advanced Clinical Applications of the Seven Core Measures for Neuroprotective Family-Centered Developmental Care, Newbord & Infant Nursing, 2016, 15 pp.
Hilary Bonifant, "A review of the effects of ageing on skin integrity and wound healing", Community Wound Care, Mar. 2019, 6 pp.
Barbara Delmore et al., "Pressure Injuries in the Pediatric Population: A National Pressure Ulcer Advisory Panel White Paper", Clincial Management, Advances in Skin & Wound Care, vol. 32, No. 9, Sep. 2019, 15 pp.
Drew Payne, Skin integrity in older adults: pressure-prone, inaccessible areas of the body, British Journal of Community Nursing, Jan. 2020, vol. 25, No. 1, 5 pp.
Neonatal Skin Care, 4th Edition, Evidence-Basked Clinical Practice Guideline, AWHONN, National Association of Neonatal Nurses, 2018, 147 pp.

\* cited by examiner

SILICONE-BASED PATIENT-SIDE ADHESIVE IN A MEDICAL SENSOR

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to the bandage of the sensor involves removal of the bandage and re-application. One example of this involves monitoring of a patient for blood oxygenation (e.g., $SpO_2$ or $rSO_2$), wherein the sensor (with particular emphasis on, for example, the disposable part of the sensor that adheres to the patient) must be removed to check the skin integrity. This can occur multiple times over a time span of a single sensor use, which can be up to 24 hours, 72 hours, or more. Accordingly, the sensor must be removed and re-adhered with minimal disruption to the patient, while still retaining sensor adherence to the skin.

Traditional pulse oximeter sensor designs utilize patient side adhesives such as acrylic or synthetic rubber adhesives. A common complaint with such sensors includes discomfort due to removal that is a frequent hospital procedure, or apparent discomfort expressed, for example by infants in Neonatal Intensive Care Units (NICUs). Another common complaint relates to loss of peel strength after the sensor removal, affecting its ability to be reapplied.

Minimal disruption to the skin is especially for patients with fragile skin, such as neonates. Disruption to the skin can occur over time as the sensor is removed multiple times or during the first removal. These disruptions can be as severe as skin tearing or just causing discomfort on removal. In neonates, for example, any added stress, such as disruption due to an adhesive bandage removal, can cause unwanted desaturation events (where the blood oxygen levels decrease) and are avoided when possible.

Accordingly, there is a need in the art for more robust medical sensors that would provide more widespread acceptance in common usage, which requires removal and re-adherence of the sensor.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting diode (LED) communicatively coupled to the communication interface and a detector, communicatively coupled to the communication interface, capable of detecting light. The patient monitoring sensor further includes a patient-side adhesive with repeatable removal and re-adherence characteristics, preventing disruption to a patient while at the same time retaining sensor adherence to the skin, the patient-side adhesive comprising a silicone adhesive.

In another aspect, the disclosure provides a patient monitoring sensor having a communication interface, through which the patient monitoring sensor can communicate with a monitor, wherein the sensor also includes a silicone patient-side adhesive that provides a peel force attachment, including after repositioning, for example in a range from about 0.5 to 0.8 N/cm from skin. In exemplary embodiments, the adhesive retains 80% of the initial peel force from skin after the $18^{th}$ removal.

In further exemplary embodiments such patient-side adhesive does not disrupt the skin (e.g., by removing only minimal skin protein) during removal, for example in a range from about 0.2 to 0.3 N/cm from skin. In exemplary embodiments, adhesives in accordance with the present disclosure such minimal protein removal is at or below 1.5 micrograms per centimeter squared ($\mu g/cm^2$). In other exemplary embodiments protein removal is at or below 5 $\mu g/cm^2$, at or below 4 $\mu g/cm^2$, at or below 3 $\mu g/cm^2$, at or below 2 $\mu g/cm^2$ or at or below 1 $\mu g/cm^2$.

Further, such exemplary silicone patient-side adhesives do not increase water loss through the skin (as measured via trans-epidermal water loss, per the below over a two hour period), for example by providing <1 $mg/cm^2$*hr increase from use. In other exemplary embodiments, adhesives in accordance with the present disclosure provide an increase of about 0.6 $g/m^2$ h from baseline (the initial measurement before the sensor is placed on the skin) for transepidermal water loss (TEWL).

In exemplary embodiments, a suitable adhesive includes silicone gel or silicone pressure sensitive adhesives with thickness between about 0.1 mm to 1.5 mm.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. The patient monitoring sensor further includes a silicone patient-side adhesive.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
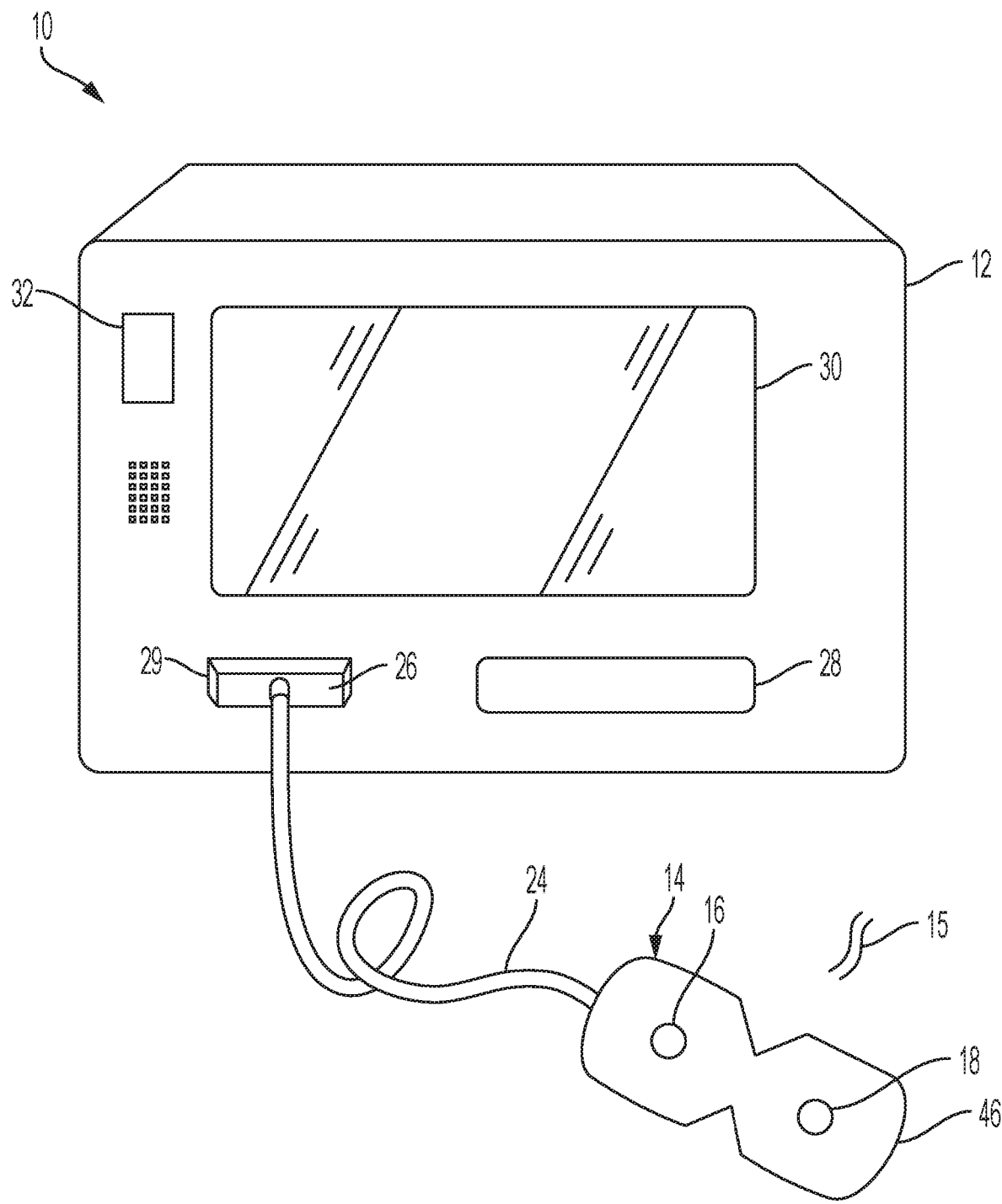
FIG. 1 illustrates a perspective view of an exemplary patient monitoring system including a patient monitor and a patient monitoring sensor, in accordance with an embodiment.

As has been noted above, traditional pulse oximeter sensor designs utilize patient side adhesives such as acrylic or synthetic rubber adhesives. A common complaint with such sensors includes discomfort due to removal that is a frequent hospital procedure, or apparent discomfort expressed, for example by infants in Neonatal Intensive Care Units (NICUs). Another common complaint relates to loss of peel strength after the sensor removal, affecting its ability to be reapplied.

The present disclosure recognizes that better adhesives for these applications may be identified, not only for comfort (gentleness), but also for the well-being of patients in situations where bandages with adhesives must not only be worn, but must also be removed and reapplied. Further, consideration of adhesives must also account for a variety of factors, including without limitation: sweat from patients; humidity of environments; contaminants on the patient-side of a sensor prior to placement; amount(s) of dead skin sloughing; smoothness (morphology) of epidermis; dwell time; variability in initial force provided by a clinician; part-to-part variation of the bandage footprint; material stability; use case duration; and reapplication time interval(s). Additional factors include possible skin integrity or residue problems upon removal.

Accordingly, the present disclosure describes a patient monitoring sensor that includes silicone patient-side adhesives provided as a part of the patient bandage, exemplary embodiments, the silicone patient-side adhesive provides a peel force attachment, including after repositioning, for example in a range from about 0.5 to 0.8 N/cm from skin. In exemplary embodiments, the adhesive retains at least 80% of the initial peel force from skin after the $18^{th}$ removal. In further exemplary embodiments, the adhesive retains at least 60% of the initial peel force from the skin after the $18^{th}$ removal. In further exemplary embodiments, the adhesive retains at least 40% of the initial peel force from the skin after the $18^{th}$ removal. In exemplary embodiments, peel force is measured according to the ASTM D3330 standard.

In further exemplary embodiments such patient-side adhesive does not disrupt the skin (e.g., by removing only minimal skin protein) during removal, for example in a range from about 0.2 to 0.3 N/cm from skin. In exemplary embodiments, adhesives in accordance with the present disclosure such minimal protein removal is at or below 1.5 micrograms per centimeter squared ($\mu m/cm^2$). In other exemplary embodiments protein removal is at or below 5 $\mu g/cm^2$, at or below 4 $\mu g/cm^2$, at or below 3 $\mu g/cm^2$, at or below 2 $\mu g/cm^2$ or at or below 1 $\mu g/cm^2$.

Further, such exemplary silicone patient-side adhesives do not increase water loss through the skin (as measured via trans-epidermal water loss), for example by providing <1 $mg/cm^2*hr$ increase from use. In other exemplary embodiments, adhesives in accordance with the present disclosure provide an increase of about 0.6 $g/m^2$ h from baseline (the initial measurement before the sensor is placed on the skin) for transepidermal water loss (TEWL).

In exemplary embodiments, a suitable adhesive includes silicone gel or silicone pressure sensitive adhesives with thickness between about 0.1 mm to 1.5 mm.

In another aspect, the disclosure provides a patient monitoring sensor having a communication interface, through which the patient monitoring sensor can communicate with a monitor, wherein the sensor also includes a patient-side silicone adhesive providing comfort, including during re-application, with minimal damage to the skin, as measured by the change to the initial rate of water loss through the skin.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector capable of detecting light. The patient monitoring sensor includes a patient-side silicone adhesive providing comfort, including during re-application, with minimal damage to the skin, as may be measured by the change to the initial rate of water loss through the skin.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, Colo.), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18 (plural detectors may be at different distances from the emitter(s)). For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. The body 46 includes a backing, or liner, provided around the emitter 16 and the detector 18, as well as an adhesive layer (not shown in FIG. 1) on the patient side. The sensor 14 may be reusable (such as a durable plastic clip sensor), disposable (such as an adhesive sensor including a bandage/liner), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
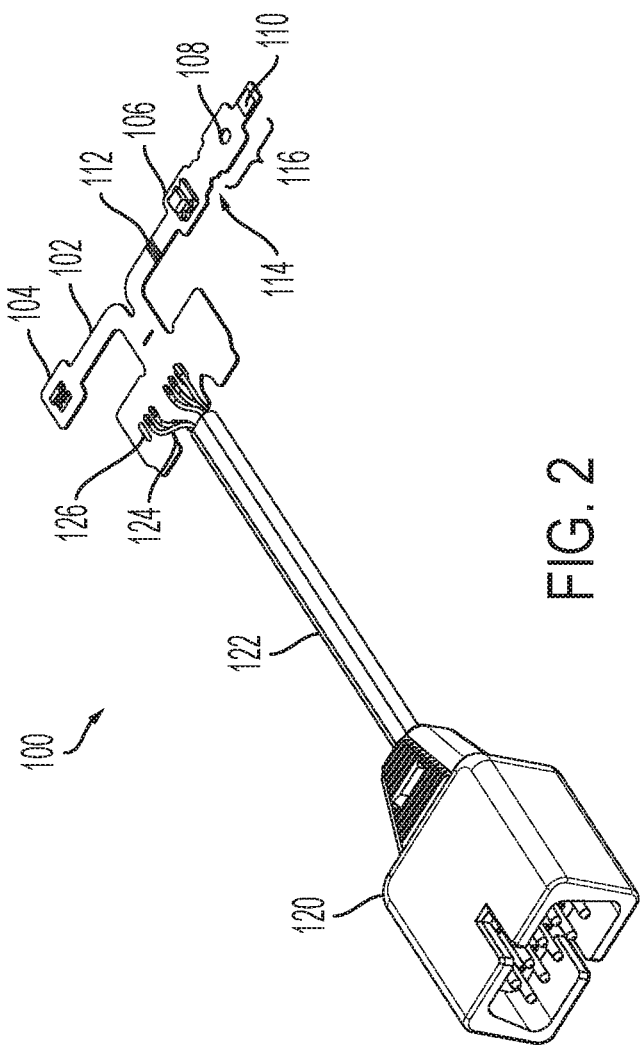
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 and a detector 106 disposed on the body 102 of the sensor 100.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106. In one embodiment, the flap portion 116 includes an adhesive 110 that is used to secure the flap portion 116 to the body 102 after the flap portion 116 is folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

In exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114.

Figure 3:
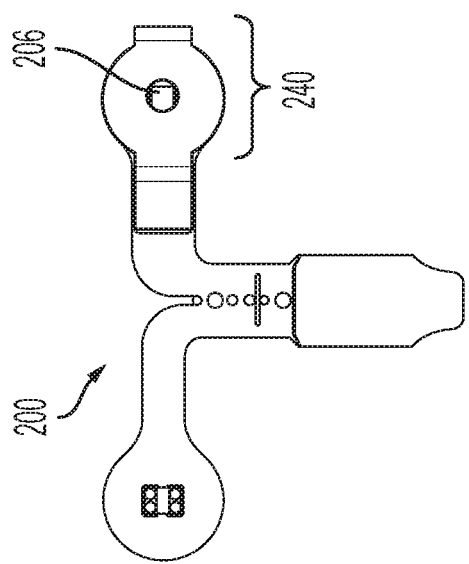
FIG. 3 illustrates a schematic view of an exemplary patient monitoring sensor, in accordance with an embodiment.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200.

As we have noted, regardless of sensor configuration particulars of the above-described exemplary embodiments, the sensor includes a silicone patient-side adhesive. Exemplary benefits of such a silicone patient-side adhesive include a peel force attachment, including after repositioning, minimization of disruption of and damage to the skin (e.g., by removing only minimal skin protein) during removal and comfort, among others.

Further, in embodiments where at least a portion of the materials used in the construction of the sensor comprise hydrophobic materials, for example including a polyester backing, such silicone patient-side adhesives contribute to hydrophobic qualities of the bandage, preventing adverse odor and a reduction of bacteria over time of use. Accordingly, such a sensor, including the silicone patient-side adhesive, will absorb less moisture from the environment, for example from a humid environment or from handwashing, etc. This provides a sensor with more longevity of use and more pleasing effects, and further results in reduction of total cost per patient by extending the useful life of the sensor.

Figure 4:
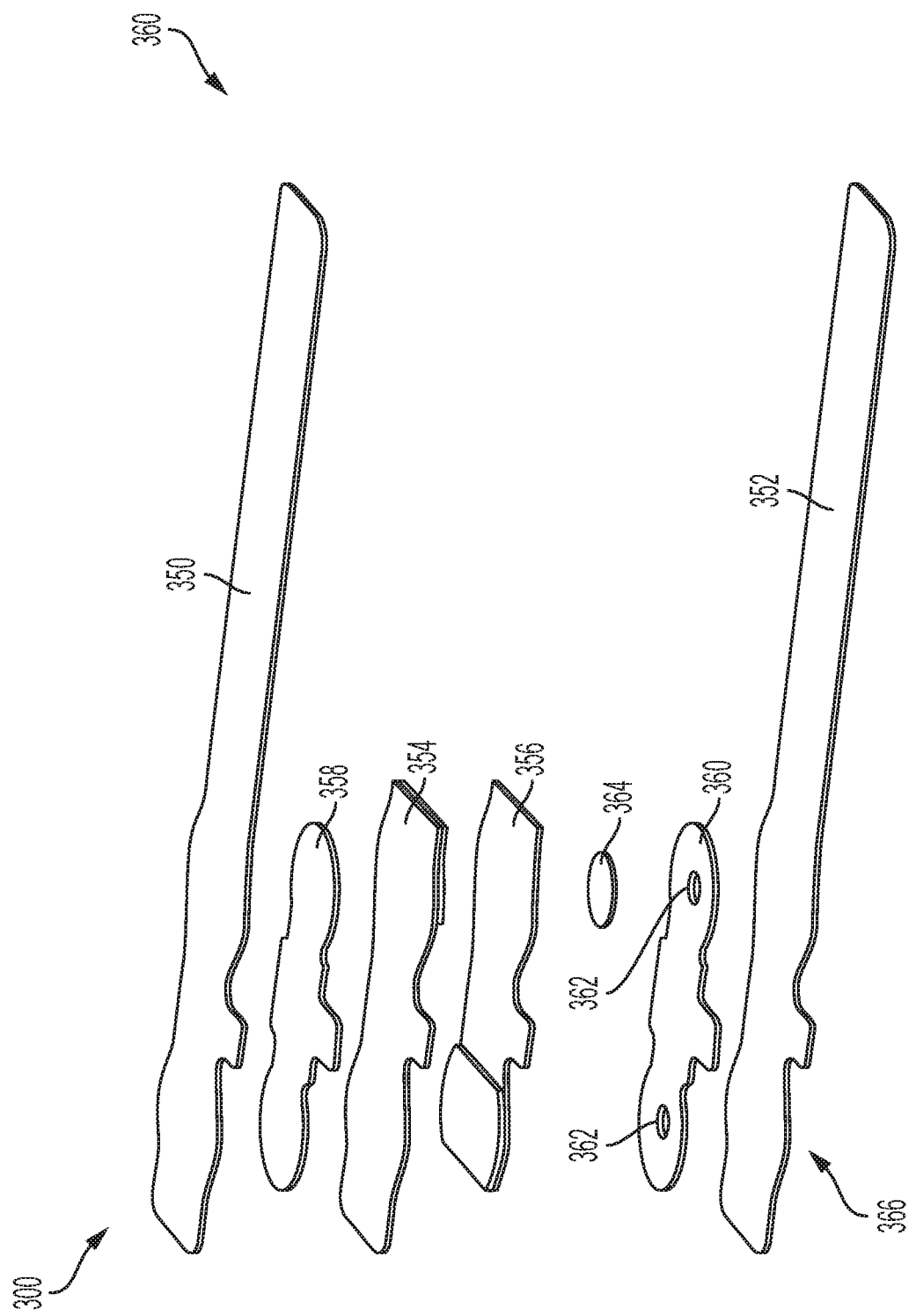
FIG. 4 illustrates a layered schematic view of an exemplary patient monitoring sensor bandage, in accordance with an embodiment.

FIG. 4 illustrates an expanded perspective view generally at 300 of an exemplary layered body/bandage configuration for a pulse oximeter sensor. The configuration includes: an upper bandage 350; an exemplary bottom tape/patient adhesive 352; exemplary top internal liner 354 and bottom internal liner 356, which in exemplary embodiments are discarded during sensor assembly, allowing the bandage to open like a leaflet to insert the flex circuit of FIGS. 2 and 3 into the bandage; a top light blocking layer, for example a metallized tape; a bottom light blocking layer 360, for example a metallized tape with holes 362 configured to allow light to shine through; and a disc 364, comprising for example a polyethylene material, configured to reduce pressure from the LED on the patient. In exemplary embodiments, bottom tape 352 comprises an adhesive layer with a release liner 366 on the patient facing side of tape 352.

Figure 5:
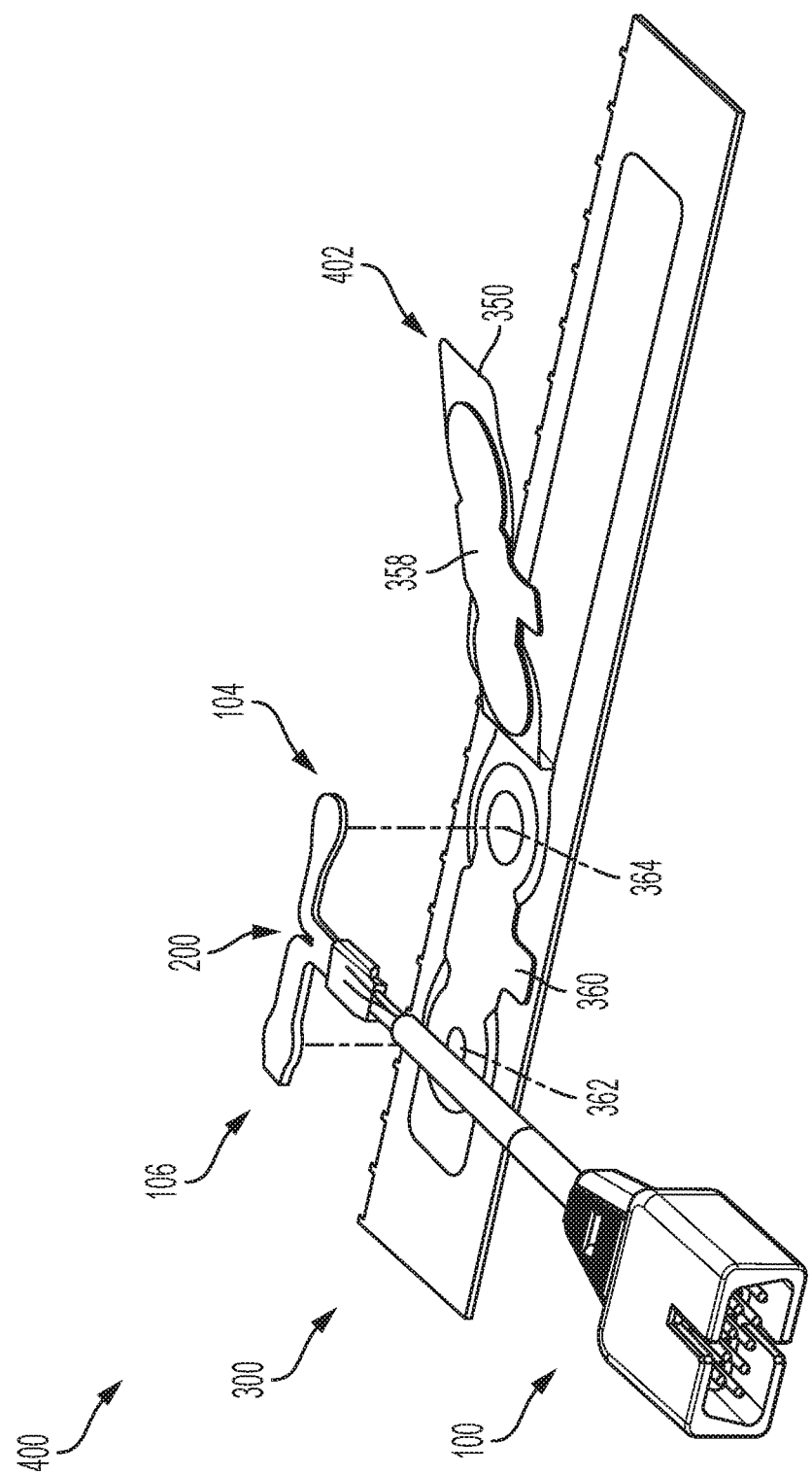
FIG. 5 illustrates a perspective view of an exemplary sensor assembly.

FIG. 5 illustrates a perspective view of exemplary assembly of the flex circuit 200 of FIGS. 2 and 3 into the bandage 300, with internal liners 354, 356 removed to allow positioning of the flex circuit 200 into the bandage, between the light blocking layers 358, 360. As is shown, detector 106 is positioned over hole 362. LED 104 is positioned over disc or ring 364 (which is positioned over another hole 362 (not shown in FIG. 5)). Rapid assembly is facilitated by removable liners 354, 356, as well as the upper bandage 350 and light blocking layer 358 acting as a foldable leaflet 402, the exemplary bandage construction provided as a sub-assembly configured to provide high-volume, fast and repeatable production of sensor assemblies.

Exemplary materials for backing material includes plastics, such as polypropylene (PP), polyester (PES), polyethylene (PE), urethanes, silicone, or the like. Additionally, various layers of the device may be constructed of one or more hydrophobic materials.

Exemplary materials for patient adhesive include gentle removal adhesives, such as various silicone adhesives that provide resilience (for re-adhesion) after repositioning, comfort, lack of water loss through patient skin (as measured via trans-epidermal water loss), which lack of water loss correlates with gentle release of the adhesive, etc.

One or more specific embodiments of the present techniques will be described below. In an effort to provide a concise description of these embodiments, not all features of an actual implementation are described in the specification. It should be appreciated that in the development of any such actual implementation, numerous implementation-specific decisions must be made, which may vary from one implementation to another.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising
a communication interface, through which the patient monitoring sensor can communicate with a monitor;
a light-emitting diode (LED) communicatively coupled to the communication interface;
a detector, communicatively coupled to the communication interface, capable of detecting light;
a bandage provided around the light-emitting, diode and the detector; and
a silicone patient-side adhesive provided on the bandage, wherein the silicone patient-side adhesive has a peel force of between about 0.5 to 0.8 N/cm from skin, including after at least one repositioning.

2. The patient monitoring sensor of claim 1, wherein the silicone patient-side adhesive also comprises a release liner.

3. Tice patient monitoring sensor of claim 1, wherein the silicone patient-side adhesive retains at least 80% of the initial peel force from skin after the $18^{th}$ removal.

4. The patient monitoring sensor of claim 1, wherein the silicone patient-side adhesive retains at least 60% of the initial peel force from skin after the $18^{th}$ removal.

5. The patient monitoring sensor of claim 1, wherein the silicone patient-side adhesive is characterized by removal of skin protein of less than 5 µg/cm^2.

6. The patient monitoring sensor of claim 1; wherein the silicone patient-side adhesive is characterized by removal of skin protein of less than 3 µg/cm^2.

7. The patient monitoring sensor of claim 1, wherein the silicone patient-side adhesive is characterized by removal of skin protein of less than about 1.5 µg/cm^2.

8. The pad ent monitoring sensor of claim 1, wherein the silicone patient-side adhesive is characterized by water loss through the skin of less than <1 mg/cm^2*hr from baseline.

9. The patient monitoring sensor of claim 1, wherein the silicone patient-side adhesive has a thickness between 0.1 mm and 1.5 mm.

10. A method for making a patient monitoring system, comprising:
   providing a communication interface; through which the patient monitoring sensor can communicate with a monitor;
   coupling a light-emitting diode (LED) communicatively to the communication interface;
   coupling a detector capable of detecting light communicatively to the communication interface;
   positioning a bandage provided around the light-emitting diode and the detector; and
   a providing a silicone patient-side adhesive on the bandage,
      wherein the silicone patient-side adhesive has a peel force of between about 0.5 to 0.8 N/cm from skin, including after at least one repositioning.

11. The method of claim 10, wherein the silicone patient-side adhesive retains at least 80% of the initial peel force from skin after the 18$^{th}$ removal.

12. The method of claim 10, wherein the silicone patient-side adhesive retains at least 60% of the initial peel force from skin after the 18$^{th}$ removal.

13. The method of claim 10, wherein the silicone patient-side adhesive retains at least 40% of the initial peel force from skin after the 18$^{th}$ removal.

14. The method of claim 10, wherein the silicone patient-side adhesive is characterized by removal of skin protein of less than 5 µg/cm^2.

15. The method of claim 10, wherein the silicone patient-side adhesive is characterized by removal of skin protein of less than 3 µg/cm^2.

16. The method of claim 10, wherein the silicone patient-side adhesive is characterized by removal of skin protein of less than about 1.5 µg/cm^2.

17. The method of claim 10, wherein the silicone patient-side adhesive is characterized by water loss through the skin of less than <1 mg/cm^2*hr from baseline.

18. The method of claim 10, wherein the silicone patient-side adhesive has a thickness between 0.1 mm and 1.5 mm.

\* \* \* \* \*